United States Patent
Paige et al.

(10) Patent No.: US 11,666,560 B2
(45) Date of Patent: Jun. 6, 2023

(54) ANTI-FIBROTIC AGENT

(71) Applicant: George Mason University, Fairfax, VA (US)

(72) Inventors: Mikell Paige, Fairfax, VA (US); Gregory Petruncio, Fairfax, VA (US); Yun Michael Shim, Charlottesville, VA (US)

(73) Assignee: George Mason University, Fairfax, VA (US)

( * ) Notice: Subject to any disclaimer, the term of this patent is extended or adjusted under 35 U.S.C. 154(b) by 0 days.

(21) Appl. No.: 17/031,183

(22) Filed: Sep. 24, 2020

(65) Prior Publication Data

US 2022/0087986 A1    Mar. 24, 2022

(51) Int. Cl.
| | | |
|---|---|---|
| C07D 225/00 | (2006.01) |
| A61K 31/436 | (2006.01) |
| A61K 31/439 | (2006.01) |
| A61P 11/00 | (2006.01) |

(52) U.S. Cl.
CPC ............ *A61K 31/439* (2013.01); *A61P 11/00* (2018.01)

(58) Field of Classification Search
CPC ...... C07D 225/00; A61K 31/436; A61K 9/00; A61P 11/00
USPC .................. 540/461, 451; 514/183
See application file for complete search history.

(56) References Cited

U.S. PATENT DOCUMENTS

| | | |
|---|---|---|
| 5,348,966 A | 9/1994 | Starzl et al. |
| 8,591,946 B2 | 11/2013 | Holm |
| 8,889,186 B2 | 11/2014 | Holm et al. |
| 8,911,777 B2 | 12/2014 | Coulter |
| 10,752,642 B1 | 8/2020 | Paige et al. |
| 2010/0086592 A1 | 4/2010 | Singh et al. |
| 2010/0297221 A1 | 11/2010 | Coulter |
| 2011/0281906 A1 | 11/2011 | Kondo et al. |
| 2011/0318277 A1 | 12/2011 | Dalby et al. |
| 2016/0296500 A1 | 10/2016 | Akoulitchev et al. |
| 2017/0072058 A1 | 3/2017 | Sheng et al. |
| 2019/0015395 A1 | 1/2019 | Appleford et al. |

FOREIGN PATENT DOCUMENTS

WO    WO 126374 A1 * 6/2019  .......... A61K 31/436

OTHER PUBLICATIONS

Rutger, A. F.; Gjaltema, B.; Van Der Stoela. M.; Bersemaa, M. B.; and Bank, R. A. Disentangling mechanisms involved in collagen pyridinoline cross-linking: The immunophilin FKBP65 is critical for dimerization of lysyl hydroxylase 2. Proc. Nall. Acad. Sci. USA 2016, 113, 7142-7147.
Nagano, J.; Iyonaga, K.; Kawamura, K.; Yamashita, A; Ichiyasu, H.; Okamoto, T.; Suga, M.; Sasaki, Y; and Koh Rogi, H., Use of tacrolimus, a potent antifibrotic agent, in bieomycininduced lung fibrosis. Eur. Respir. J_2006, 27, 460-9.
Lemons, P.A.; Gladstone, B. G.; Seth, A.; Chao, E. D.; Foley, M.A.; Schreiber, S. L. Synthesis of alcineurin-Resistant Derivates of FK506 and Selection of Compensatory Receptors. Chemistry & Biology, 2002, 9. 19-61.
Ertl, P.; Rohde, B.; and Selzer, P. Fast Calculation of Molecular Polar Surface Area as a Sum of Fragment-Based Contributions and Its Application to the Prediction of Drug Transport Properties. J_Med. Chem., 2000, 43, 3714-3717.
Shivshankar. Journal of Drug Delivery Science and Technology, 2014, 24(5), 469-77.
Perren. Neurobiology of Aging, 2014, 36, 1559-68.
Balakin. Current Drug Discovery Technologies, 2005, 2, 99-113.
Non-Final office action issued for the U.S. Appl. No. 16/399,357, dated Feb. 4, 2020, 5 pages.
Notice of Allowance issued for the U.S. Appl. No. 16/399,357, dated May 20, 2020, 5 pages.

* cited by examiner

*Primary Examiner* — Charanjit Aulakh
(74) *Attorney, Agent, or Firm* — Dave Law Group LLC; Raj S. Dave

(57) ABSTRACT

Tacrolimus is an immunosuppressant drug. The present disclosure provides an anti-fibrotic agent by transforming Tacrolimus, such that the anti-fibrotic agent is used for treating fibrosis. The anti-fibrotic agent is not immunosuppressant. In one embodiment, the present invention provides a method to transform Tacrolimus into an anti-fibrotic agent.

12 Claims, 3 Drawing Sheets

ANTI-FIBROTIC AGENT

FIELD OF THE INVENTION

This invention relates to a compound to treat fibrosis, more particularly to Idiopathic pulmonary fibrosis (IPF). In one embodiment, the invention relates to a method to produce the compound to treat fibrosis.

BACKGROUND OF INVENTION

Fibrosis is defined by the overgrowth, hardening, and/or scarring of various tissues and is attributed to excess deposition of extracellular matrix components including collagen (1). Fibrosis is aftermath of chronic inflammatory reactions induced by a variety of stimuli including persistent infections, autoimmune reactions, allergic responses, chemical insults, radiation, and tissue injury (2). Different types of fibrosis include Idiopathic pulmonary fibrosis, liver cirrhosis, systemic sclerosis, progressive kidney disease, and cardiovascular fibrosis (3). Idiopathic pulmonary fibrosis (IPF) is the most common and deadly form of idiopathic interstitial pneumonia (4).

IPF is defined as a chronic lung disease characterized by a progressive and irreversible decline in lung function due to fibrosis. It is a disease where the lungs become fibrotic and the patient can no longer breathe. "IPF accounts for approximately 55% of all idiopathic interstitial pneumonias (IIP) and 25% of all interstitial lung diseases (ILD) with about 35,000 new diagnoses per year in Europe and 5 million in the world. It is a disabling and fatal disease with a poor prognosis. Five-year survival is 20-40%, which is lower than for breast cancer, colorectal cancer and pulmonary arterial hypertension." Patients with IPF usually die within 3 to 5 years, and there is no effective therapy to cure patients. The mortality from diagnosis is estimated between 3 and 5 years, and onset of the disease usually occurs in elderly adults.

Because there is no known cure, the goal of IPF treatment is to stabilize or reduce the rate of disease progression.

Treatment of IPF includes the use of corticosteroids, N-acetylcysteine, gastroesophageal reflux medications, endothelin-receptor antagonists, phosphodiesterase-5 inhibitors, pirfenidone, and nintedanib (5). Pirfenidone and nintedanib are widely used medications for treatment of IPF. Pirfenidone (Esbriet®, Pirfenex®, Pirespa®) and nintedanib (OFEV®) are two drugs approved to treat IPF in many countries around the world. The combination treatment with pirfenidone and nintedanib have also been suggested.

U.S. Ser. No. 10/450,258B2 discloses the substituted aromatic compounds for the treatment of various types of fibrosis. US20160025745A1 discloses the methods of diagnosing and treating a fibrotic condition in a mammalian subject. Further, US20180303828A1 discloses a unit dose of an MDM2 inhibitor that provides long-lasting relief from IPF and other Pulmonary conditions by selectively removing senescent cells from the lung. US 2020/0121625 discloses a combination therapy for the treatment of inflammatory, metabolic, fibrotic and cholestatic diseases. US 2020/0061028 describes novel combinations of (i) NTZ or an analogue thereof, and (ii) an anti-NASH, anti-fibrotic or anti-cholestatic agent, and their use in therapy, in particular in the treatment of inflammatory, metabolic, fibrotic and cholestatic diseases.

Despite extensive investigation, the cause of IPF remains unknown. The fibrosis in IPF has been linked to cigarette smoking, environmental factors (e.g. occupational exposure to gases, smoke, chemicals or dusts), other medical conditions including gastroesophageal reflux disease (GERD), or to genetic predisposition (familial IPF). However, none of these is present in all people with IPF and therefore do not provide a completely satisfactory explanation for the disease. The prevalence of IPF has been estimated between 14.0 and 42.7 per 100,000 persons based on a USA analysis of healthcare claims data, with variation depending on the case definitions used in this analyses.

The goal of present invention is to provide a treatment for IPF, essentially to reduce the symptoms, stop disease progression, prevent acute exacerbations, and prolong survival.

SUMMARY OF INVENTION

The technology in the present invention is to stop or possibly reverse fibrosis in patients that suffer from IPF.

An embodiment relates to a method comprises administering a compound in a subject, wherein the compound is configured to reduce fibrosis in the subject, wherein the compound comprises a FKBP binding domain and a blocked calcineurin binding domain.

In an embodiment, the compound is represented by a Formula II

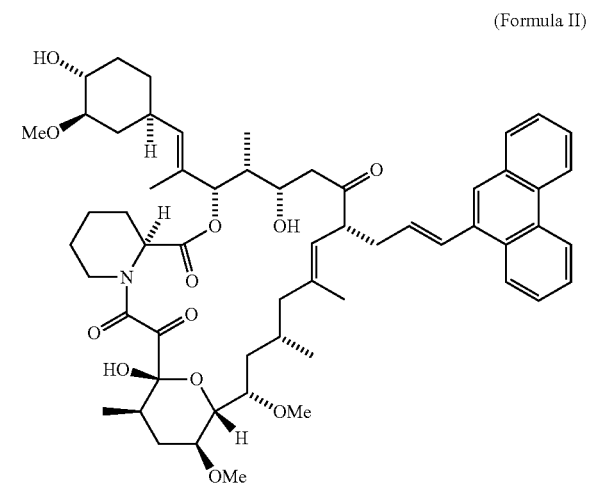 [SMILES: CO[C@H]1C[C@@H](C)C/C(C)=C/[C@@H](C/C=C/c2cc3ccccc3c3ccccc23)C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]1[C@@H](OC)C[C@H]2C]

(Formula II)

In an embodiment, the compound is not an immunosuppressant.

In an embodiment, the compound is configured to inhibit a peptidyl-prolyl cis/trans isomerase (PPIase) macrophage infectivity potentiator (MIP).

In an embodiment, the compound comprises a solvent accessible region.

In an embodiment, the compound is synthesized by transforming of FK-506 and/or Fk-506 analogue using a Heck reaction.

In an embodiment, the compound is configured to solubilize collagen in the subject.

In an embodiment, a compound comprising a FKBP binding domain and a blocked calcineurin binding domain, wherein the compound is configured to reduce fibrosis in the subject.

In an embodiment, the Heck reaction is carried in a reaction mixture comprising the FK-506 or its analogue and an unsaturated halide in presence of a Pd catalyst.

In an embodiment, the Heck reaction is carried within a temperature range of about 60° C. to about 120° C.

In an embodiment, the product is extracted from the reaction mixture and then purified to get a purified product.

In an embodiment, yield of purified product is within a range of about 50 to about 95%.

In an embodiment, the compound with Formula II is configured to inhibit FKBP65 and/or FKBP12.

DETAILED DESCRIPTION

Definitions and General Techniques

Figure 1:
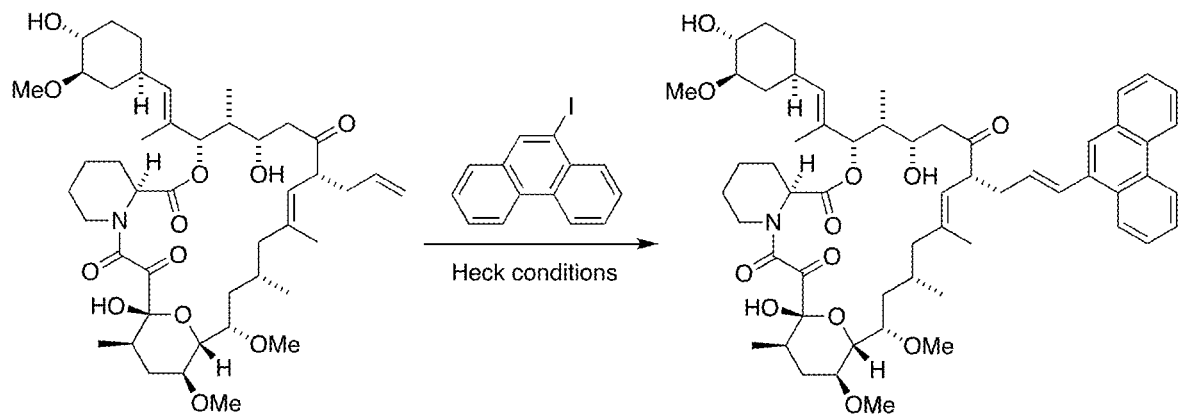
FIG. 1 shows the synthesis of CT-474 from FK-506 by traditional Heck reaction. The reactant is FK-506 and the product is CT474.

The following description is made for the purpose of illustrating the general principles of the present invention and is not meant to limit the inventive concepts claimed herein. Further, particular embodiment described herein can be used in combination with other described embodiments in each of the various possible combinations and permutations.

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

For simplicity and clarity of illustration, the drawing figures illustrate the general manner of construction, and descriptions and details of well-known features and techniques may be omitted to avoid unnecessarily obscuring the present disclosure. Additionally, elements in the drawing figures are not necessarily drawn to scale. For example, the dimensions of some of the elements in the figures may be exaggerated relative to other elements to help improve understanding of embodiments of the present disclosure. The same reference numerals in different figures denotes the same elements.

The present invention may be embodied in other specific forms without departing from its spirit or characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The methods and techniques of the present invention are generally performed according to conventional methods well known in the art and as described in various general and more specific references that are cited and discussed throughout the present specification unless otherwise indicated. The nomenclatures used in connection with, and the procedures and techniques of embodiments herein, and other related fields described herein are those well-known and commonly used in the art.

To facilitate understanding of the invention, a number of terms and abbreviations as used herein are defined below as follows:

When introducing elements of the present invention or the preferred embodiment(s) thereof, the articles "a", "an", "the" and "said" are intended to mean that there are one or more of the elements.

The terms "comprising", "including" and "having" are intended to be inclusive and mean that there may be additional elements other than the listed elements. Each embodiment disclosed herein can comprise, consist essentially of or consist of its particular stated element, step, ingredient or component.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, Band/or C" is intended to mean A alone, B alone, C alone, A and B in combination, A and C in combination, B and C in combination or A, B, and C in combination.

As defined herein, "approximately", "about" can, in some embodiments, mean within plus or minus ten percent of the stated value. In other embodiments, "about" can mean within plus or minus five percent of the stated value. In further embodiments, "about" can mean within plus or minus three percent of the stated value. In yet other embodiments, "about" can mean within plus or minus one percent of the stated value.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 50% to 70% should be considered to have specifically disclosed sub-ranges such as from 50 to 52, from 50 to 55, from 55 to 60, from 60 to 65, from 60 to 70, from 67 to 70, from 66 to 70 etc., as well as individual numbers within that range, for example, 50, 52, 55, 62, 63, 67 etc. This applies regardless of the breadth of the range.

As used herein, phrase "have formula" or "there is structure" or "represented by formula" be not intended to have it is restricted and with Essential Terms "bag Containing" identical mode uses. For example, if unless otherwise stated, depicting a kind of structure, then it should be understood that all In stereoisomer and tautomeric forms are encompassed by.

Definitions

Fibrosis: Fibrosis is defined by the overgrowth, hardening, and/or scarring of various tissues and is attributed to excess deposition of extracellular matrix components including collagen. The key cellular mediator of fibrosis is the fibroblast such as myofibroplast, which when activated serves as the primary collagen-producing cell.

Anti-fibrotic agent: It is a class of medications which are used to treat or reduce the effects of fibrosis.

Reduce Fibrosis: As used herein, the term signifies that the fibrosis after the administration of an agent has decreased or has reduced the progression of fibrosis in the subject. In an embodiment reduction can vary from at least about 10%, at least about 20%, at least about 30%, at least about 40%, at least about 50%, at least about 60%, at least about 70%, at least about 80%, at least about 90% or more.

Treatment: Treatment is broadly defined as an attempted remediation of a health problem such as but not limited to reduce the symptoms, stop disease progression, prevent acute exacerbations, and prolong survival of IPF patients. Treatment and therapy are generally considered synonyms. "Treat" or "treatment" are used interchangeably through-out the specification.

Calcineurin: Calcineurin is an enzyme that activates T-cells of the immune system. T-cells (also called T-lymphocytes) are a type of white blood cell that play a key role in cell-mediated immunity.

Calcineurin binding domain: Domain is a functional and/or structural unit of a protein. A binding domain broadly defined as a structural unit of the protein that posse's ability to bind with the desired target, such as a calcineurin binding domain would bind to calcineurin. Upon binding of calcineurin with the calcineurin binding domain there is conformational change in calcineurin, leading to series of down reaction.

Catalyst: Catalysis is the process of increasing the rate of a chemical reaction by adding a substance known as a catalyst, which is not consumed in the catalyzed reaction and can continue to act repeatedly.

FK506: is the active ingredient in Tacrolimus®. FK-506 and FK506 are used interchangeably throughout the specification.

Immunosuppression: Immunosuppression is a reduction of the activation or efficacy of the immune system. Reduction of Immune system can vary from at least about 10%, at least about 20%, at least about 30%, at least about 40%, at least about 50%, at least about 60%, at least about 70%, at least about 80%, at least about 90% or more.

Immunosuppressive agent: A medication or drugs that depresses or halts immune system activity. Some of these drugs are used to make the body less likely to reject a transplanted organ, such as a liver, heart, or kidney. For example, such as calcineurin inhibitors such as Tacrolimus and Cyclosporine. Tacrolimus drug is used as an immunosuppressant primarily in liver and kidney transplantations, although in some clinics it is used in heart, lung, and heart/lung transplantations. "Immunosuppressive agent" or "Immunosuppressant" is used interchangeably through-out the specification.

Calcineurin inhibitors: Molecules which inhibit the action of calcineurin, such as but not limited to cyclosporine, voclosporin, pimecrolimus and tacrolimus and their analogs with the similar function of binding to calcineurin.

Not immunosuppressant: As used herein, the term is defined as with a reduced ability to inhibit T cells or immune activity compared to FK506. In an embodiment, the reduced ability can vary from at least about 10%, at least about 20%, at least about 30%, at least about 40%, at least about 50%, at least about 60%, at least about 70%, at least about 80%, at least about 90% or more.

Reduced immune suppress activity: As used herein, the term is defined as suppression of immune response is less compared to FK506. In an embodiment, less can vary from at least about 10%, at least about 20%, at least about 30%, at least about 40%, at least about 50%, at least about 60%, at least about 70%, at least about 80%, at least about 90% or more.

IPF: Idiopathic pulmonary fibrosis (IPF) is a chronic lung disease where the lungs become fibrotic and characterized by a progressive and irreversible decline in lung function due to fibrosis due to which the patient can no longer breathe. Patients with IPF usually die within 3 to 5 years of diagnosis. Other names for IPF includes cryptogenic fibrosing alveolitis, idiopathic fibrosing alveolitis (chronic form), usual interstitial pneumonia.

Small molecule: refers to an organic compound usually smaller than 1 KDa in molecular weight that is used to modulate a biological system.

PPIase: PPIases catalyze the cis to trans isomerization of certain proline imidic bonds in proteins. Two families of PPIases are the FK506 binding proteins (FKBPs), and cyclophilins (CyPs). The active site of PPIases is shallow and solvent exposed. Each of the PPIases contains at least one PPIase domain. This domain is composed of antiparallel β-sheets that position a short α-helix. A shallow groove between the α-helix and β-sheets forms a solvent-exposed active site that binds to the target proline. The PPIase activity of FKBPs is inhibited by binding to agents. The agents may be immunosuppressants such as but not limited to FK506 or rapamycin.

PPIase binding domain: It is defined as a Peptidyl-Proline Isomerases binding domain.

Synthetic route: Chemical transformation one compound into another compound.

Transformation: means chemical transformation of a chemical substance to another chemical substance.

Heck's reaction: It is (also called the Mizoroki-Heck reaction) is the chemical reaction way to substitute alkenes.

Alkyl: means an aliphatic hydrocarbon group that can be linear or branched acyclic or cyclic and comprises 1 to 25 carbon atoms in the chain. In one embodiment, useful alkyl groups comprise 1 to 12 carbon atoms in the chain. "Branched" means that one or more lower alkyl groups such as methyl, ethyl or propyl, are attached to a linear alkyl chain. The alkyl group can contain one or more heteroatoms selected from F, O, N, and Si. Non-limiting examples of suitable alkyl groups include methyl, ethyl, n-propyl, isopropyl, n-butyl, t-butyl, n-pentyl, hexyl, heptyl, nonyl, decyl, cyclohexyl and cyclopropylmethyl.

Aryl: means an aromatic monocyclic or multicyclic ring system comprising 5 to 14 carbon atoms, preferably 6 to 10 carbon atoms. The aryl group can contain one or more heteroatoms selected from F, O, N and Si. The aryl group can be substituted with one or more "ring system substituents" which may be the same or different and include hydrocarbyl substituents. Non-limiting examples of suitable aryl groups include phenyl, naphthyl, indenyl, tetrahydronaphthyl and indanyl.

Aralkyl or arylalkyl means an aryl-alkyl-group in-which both aryl and alkyl are as previously described. In some embodiments, useful aralkyls comprise a lower alkyl group. Non-limiting examples of such suitable aralkyl groups include benzyl, phenethyl and naphthlenylmethyl where the aralkyl is linked to the norbornene through the alkylene group. In some embodiments, the aralkyl group can contain one or more heteroatoms selected from F, O, N and Si.

Halogen refers to F, Cl. Br, and I.

CT474: The anti-fibrotic agent to treat IPF. The agent formed by transforming FK506 using Heck's reaction. The term CT-474 or CT474 are used interchangeably throughout the specification.

Extraction: It is the first step to separate the desired products from the reacted reaction mixture. Extraction methods include solvent extraction, distillation method, pressing and sublimation according to the extraction principle. Solvent extraction is the most widely used method. The selection of the solvent is crucial for solvent extraction. Selectivity, solubility, cost and safety should be considered in selection of solvents. Based on the law of similarity and intermiscibility (like dissolves like), solvents with a polarity value near to the polarity of the solute are likely to perform better and vice versa. Extraction produces an extracted product. The extracted product can also be called as crude product.

Crude product is defined as an unrefined or unpurified product produced from the transformation of FK506 to CT474. The crude product may contain product of interest (which herein in CT474) and many contaminating or undesired substances along with it. Purification of crude product help in separating the product of interest from undesired substances.

Purified Product: The product obtained after purification of crude product.

Yield is defined as a measure of a chemical reaction's efficiency. In an embodiment, yield is ratio of moles of purified product to moles of the limiting reactant. In an embodiment, the yield is expressed in percentage.

Subject refers to an animal, a non-human mammal, or a human. A subject in need refers to a patient.

MIC: the minimum or minimal inhibitory concentration (MIC) is the lowest concentration of a chemical, usually a drug, which prevents visible growth of a bacterium or bacteria.

Tacrolimus analogue: Analogue is broadly defined as a compound with a molecular structure closely similar to that of another. For example, but not limited to FK506 analogues are FK520, dihydrotacrolimus, FK523, FK525 or the like are known, in which FK520 is a 23-membered macrolide compound and an ethyl analog of FK506, dihydrotacrolimus is a C21-propyl analogue of FK506, FK523 is a C21-methyl analogue of FK-506, and FK-525 is a prolyl analogue of FK506. Other analogoues may be 31-O-demethyl-FK506, 9-deoxo-FK506, 9-deoxo-31-O-demethyl-FK506, and 9-deoxo-prolyl-FK506. As used herein, Tacrolimus analogue is also called as FK506 analogue.

Inhibit as used herein is broadly defined to restrain biological activity. In an embodiment, inhibition can vary from at least about 10%, at least about 20%, at least about 30%, at least about 40%, at least about 50%, at least about 60%, at least about 70%, at least about 80%, at least about 90% or more.

Collagen: Collagen is the main structural protein in the extracellular matrix in the various connective tissues in the body. Collagen consists of amino acids bound together to form a triple helix of elongated fibril known as a collagen helix. The collagen helix is stabilized by many hydrogen bonds. The fibroblast is the most common cell that creates collagen. Fibroblast associated with fibrosis is myofibroblast.

Prevention of Stabilization of Collagen as used herein is broadly defined as an ability to decrease the deposition of collagen. In an embodiment, the deposition of collagen can be inhibited by reducing the proliferation and activation fibroblast or actively induce myofibroblast apoptosis.

The embodiments of this invention relate to various features (F):
F1: CT474 for treating IPF.
F2: Anti-fibrotic drug that is not immunosuppressant.
F3: Transformation of FK506 to CT474.
F4: Compounds having calcineurin binding domain blocked.
F5: Compounds inhibit peptidyl-prolyl cis/trans isomerase (PPIase) macrophage infectivity protentiator (MIP) protein.

In IPF, the scarring of the walls of alveoli makes it thicker which makes it harder for oxygen to pass into the blood. The word "Idiopathic" in IPF signify 'of unknown cause'. Some risk factors accountable for the IPF include smoking, acid reflux, bacterial and viral infections, exposure at work places, a family history of pulmonary fibrosis, presence of certain genes such as MUC5B, TERT, TERC, DKC1, RTEL1, AKAP13, DSP, FAM13A, DPP9, and TOLLIP.

Many patients with idiopathic pulmonary fibrosis (IPF) undergo hospitalizations due to pulmonary infections. Gram-negative bacteria are the most common pathogens isolated from patients with IPF who are hospitalized for pulmonary infections. Bacteria held responsible for IPF are *Haemophilus influenzae, Pseudomonas aeruginosa, Staphylococcus aureus, Branhamella catarrhalis*, and *Klebsiella pneumoniae. Klebsiella pneumoniae* is a common cause of nosocomial pneumonia.

In an embodiment, the invention is to stop or possibly reverse fibrosis in patients that suffer from IPF.

Tacrolimus® is an immunosuppressive drug. Immunosuppressive drugs, also known as immunosuppressive agent, immunosuppressants and antirejection medications. These drugs inhibit or prevent activity of the immune system.

Tacrolimus® also known Fujimycin is a product of the bacterium *Streptomyces tsukubaensis*. It is a macrolide lactone and acts by inhibiting calcineurin. The drug is used primarily in liver and kidney transplantations, although in some clinics it is used in heart, lung, and heart/lung transplantations. It reduces peptidyl-prolyl isomerase activity by binding to FKBP12 (FK506 binding protein) creating a new complex. This FKBP12-FK506 complex inhibits calcineurin which inhibits T-lymphocyte signal transduction and IL-2 transcription. It prevents cell from transitioning from the G0 into G1 phase of the cell cycle. Tacrolimus also prevents the dephosphorylation and translocation of nuclear factor of activated T-cells (NF-AT), a nuclear component thought to initiate gene transcription for the formation of lymphokines. Tacrolimus also inhibits the transcription for genes such as that encode IL-3, IL-4, IL-5, GM-CSF, and TNF, all of which are involved in the early stages of T-cell activation. Additionally, tacrolimus has been shown to inhibit the release of pre-formed mediators from skin mast cells and basophils, and to downregulate the expression of FceRI on Langerhans cells.

The common problem of many immunosuppressive drugs is immunodeficiency. The immunosuppressive drugs act non-selectively, resulting in increased susceptibility to infections and decreased cancer immunosurveillance. Immunosuppressive drugs also cause other side-effects, such as hypertension, dyslipidemia, hyperglycemia, peptic ulcers, lipodystrophy, moon face, liver and kidney injury. The immunosuppressive drugs interact with other medicines and affect their metabolism and action.

FK506 is an active ingredient in Tacrolimus®. Therefore, Tacrolimus is also known as FK506. However, the immunosuppression function of FK506 prevents its use as an anti-fibrotic.

In an embodiment, the present invention relates to making a new analog of FK506 that does not cause immunosuppression. In an embodiment, the present invention relates to development of new analog of FK506 that can be used as anti-fibrotic and do not cause immunosuppression. In an embodiment, the present invention relates to development of new analog of FK506 with a reduced immune suppression activity but with retained FKBP binding activity. The new analog is CT474.

In an embodiment, the FK506 is transformed to CT474.
The FK506 is represented by Formula I.

(Formula I)

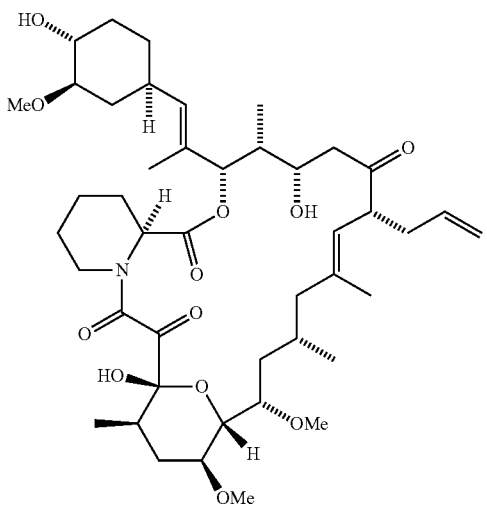

CT474 is represented by a Formula II (Formula II)

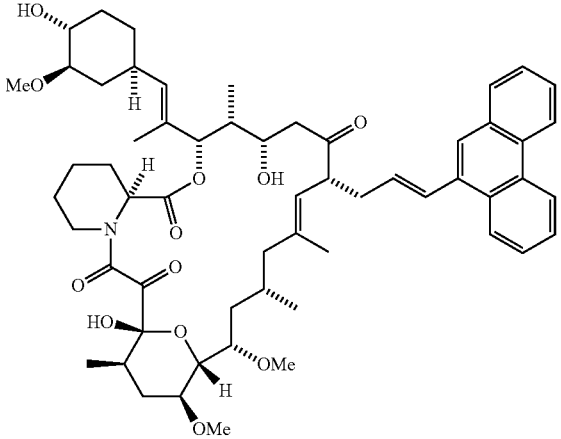

The "OH" represents hydroxyl group, "OMe" represents methoxy group, "H" represent Hydrogen, "0" represents oxygen, "N" represents nitrogen.

In an embodiment, CT474 is used for therapeutically targeted treatment of fibrosis, more preferably for treatment of IPF in a subject.

In an embodiment, CT474 comprises a blocked calcineurin binding domain.

Calcineurin activates nuclear factor of activated T cell cytoplasmic (NFATc), a transcription factor, by dephosphorylating it. The activated NFATc is then translocated into the nucleus, where it upregulates the expression of interleukin 2 (IL-2), which, in turn, stimulates the growth and differentiation of the T cell response. Calcineurin is the target for a class of drugs called calcineurin inhibitors. Calcineurin inhibitors have calcineurin binding domain to inhibit the action of calcineurin. Calcineurin inhibitors suppress the immune system.

Tacromilus or its active ingredient FK506 is immunosuppressant. FK506 has calcineurin binding domain.

Figure 4:
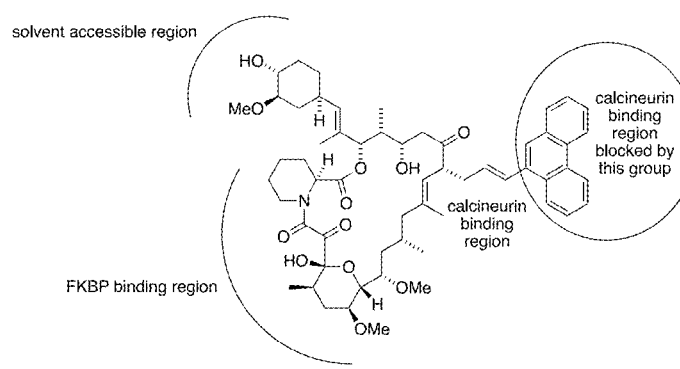
FIG. 4 shows blocked calcineurin binding domain in CT474.

In CT474, the compound described in the present disclosure and prepared from FK506 is not immunosuppressive. The FIG. 4 shows blocked calcineurin binding domain in CT474.

In an embodiment, CT474 comprises a PPIase binding domain.

PPIases are involved in a plethora of biological processes, such as gene expression, signal transduction, protein secretion, development, and tissue regeneration. PPIases catalyze the isomerization of proline, acting as a regulatory switch during folding, activation of many proteins. These proteins have shown key roles in cancer, neurodegeneration, and psychiatric disorders.

PPIase are present in Bacteria, Protozoa, Fungi, Plantae and Animalia. In an embodiment, PPIase may help to regulate proteins associated with many pathogens. The extent of contribution to virulence is highly variable and dependent on the pleiotropic roles of a single PPIase in the respective pathogen.

In an embodiment, PPIase inhibitors are important therapeutics. PPIase inhibitors have PPIase binding domain to inhibit the action of PPIase.

In an embodiment, CT474 has a binding domain or region for FKBP. CT474 does not suppress immune response. In an embodiment, CT474 has reduced immune suppress activity.

FKBP binding region binds FKBP. The binding of FKBP binding region with FKBP can be used to manipulate protein localization, signaling pathways and protein activation.

In an embodiment, FKBPs are present in mammals such as humans as well as microbes. In humans FKBPs are associated with many diseases. Human FKBPs can be subdivided into four groups: the cytoplasmic, endoplasmic reticulum, nuclear, and TPR (tetratricopeptide repeats)-containing FKBPs. There are five members of the FKBP family which are named according to their calculated molecular masses (FKBP12, FKBP13, FKBP25, FKBP52, and FKBP65).

In an embodiment, CT474 bind with the human FKBP. In an embodiment, CT474 binds with FKBP12 and/or FKBP13 and/or FKBP25 and/or FKBP52 and/or FKBP65.

In an embodiment, PPIases in bacteria are associated with virulence. PPIase in bacteria belong to soluble PPIases and membrane bound PPIase. Soluble PPIases are either cytosolic or periplasmic in gram-negative bacteria, and some of them are secreted extracellularly. Membrane-bound bacterial PPIases can face the exterior environment or the interior periplasm depending on the membrane in which they are anchored.

In an embodiment, Macrophage infectivity potentiator (MIP) like PPIases are virulence-associated, secreted, and, typically, outer membrane-localized FK506 Binding Proteins of Gram-negative bacteria.

In an embodiment, CT474 binds with microbial PPIase. The 'microbe' used herein is defined as tiny living things that are found all around us and are too small to be seen by the naked eye. Microbes could be bacteria, fungi, algae and/or protists. In an embodiment, CT474 binds with the microbial FKBP. In an embodiment, CT474 binds with the bacterial FKBP. In an embodiment, CT474 binds with the fungal FKBP. In an embodiment, CT474 has anti-bacterial activity. In an embodiment, CT474 has anti-fungal activity. In an embodiment, CT474 has anti-microbial activity. In an embodiment, CT474 has anti-insecticidal activity. The term 'anti-microbial' signify is an agent that kills microorganisms or stops their growth. Similarly, anti-bacterial, anti-fungal, anti-insecticidal define an agent that kills or stops the growth of bacteria, fungi and insect respectively. The agent stop the growth of microbe or bacteria or fungi or insect by more than about 60%, about 70%, about 75%, about 80%, about 90% or more.

In one embodiment of the present disclosure, CT474 is configured to inhibit a peptidyl-prolyl cis-trans isomerase (PPIase) macrophage infectivity protentiator (MIP).

In an embodiment, CT474 has suppressive effects on gram negative bacteria responsible for IPF, such as but not limited to *Haemophilus influenzae, Pseudomonas aeruginosa, Staphylococcus aureus, Branhamella catarrhalis*, and *Klebsiella pneumoniae.*

In an embodiment, CT474 has a suppressive effect on *Klebsiella pneumoniae.*

In an embodiment, the minimum concentration of CT474 that can inhibit or suppress the growth of *Klebsiella pneumoniae* (MIC) is 5 nm, 10 nm, 50 nm, 100 nm, 150 nm, 200 nm, 300 nm, 500 nm, 750 nm, 1 μm, 2 μm, 3 μm, 4 μm, 5 μm, 6 μm, 7 μm, 8 μm, 9 μm, 10 μm, 15 μm, 20 μm and more.

In an embodiment, the minimum concentration of CT474 that can inhibit or suppress the growth of gram negative bacteria responsible for IPF, such as but not limited to *Haemophilus influenzae, Pseudomonas aeruginosa, Staphylococcus aureus, Branhamella catarrhalis*, and *Klebsiella pneumoniae* is 5 nm, 10 nm, 50 nm, 100 nm, 150 nm, 200 nm, 300 nm, 500 nm, 750 nm, 1 μm, 2 μm, 3 μm, 4 μm, 5 μm, 6 μm, 7 μm, 8 μm, 9 μm, 10 μm, 15 μm, 20 μm and more.

In an embodiment, CT474 concentration and suppressive property to inhibit or suppress the growth of gram negative bacteria responsible for IPF, such as but not limited to *Haemophilus influenzae, Pseudomonas aeruginosa, Staphylococcus aureus, Branhamella catarrhalis*, and *Klebsiella pneumoniae* are in positive correlation. The positive correlation signifies that with increasing concentration of CT474 the suppressive property to inhibit the growth of gram negative bacteria also increases.

In an embodiment, CT474 concentration and suppressive property to inhibit or suppress the growth of *Klebsiella pneumoniae* are in positive correlation. The positive correlation signifies that with increasing concentration of CT474 the suppressive property to inhibit the growth of *Klebsiella pneumoniae* also increases.

In an embodiment, increase in concentration of CT474 from 10 nM upto 1 μM concentration, there is consecutive decrease in colony forming units (CFU) of the microorganism, *Klebsiella pneumoniae.*

In an embodiment, CT474 can inhibit growth of any bacteria possessing PPIase such as but not limited to gram negative bacteria.

In an embodiment, CT474 can inhibit growth of any microbe possessing PPIase such as but not limited to gram negative bacteria.

In an embodiment, CT474 comprises a solvent accessible region. The solvent accessible region helps in proper protein folding. In an embodiment, CT474 comprises of FKBP binding region and solvent accessible region as shown in FIG. 4

In an embodiment, the present disclosure demonstrates the method to prepare CT474 from FK-506. The FK506 is represented by Formula I.

(Formula I)

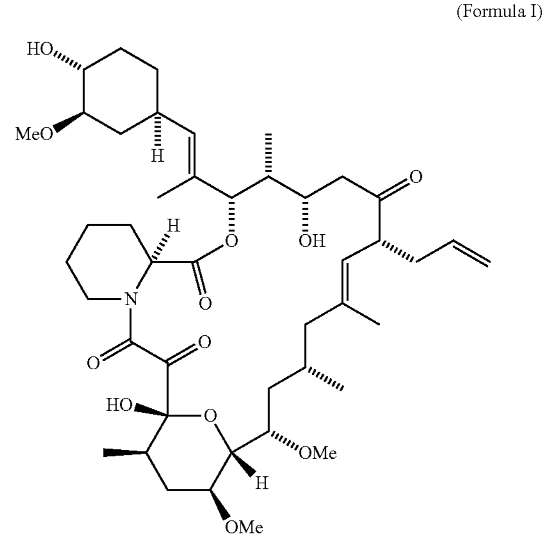 [SMILES: C=CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]

In an embodiment of the present invention, the method to prepare CT474 from FK506 follow Heck's reaction. In an embodiment, FK506 is reacted with unsaturated halide in presence of catalyst(s) to obtain a crude product. In an embodiment, the crude product can be diluted.

In an embodiment, step of the present invention is: FK506 and unsaturated halide are dissolved in the solution of organic solvent and organic bases, add palladium catalyst and part then, rise to the suitable temp reaction gradually, after reaction finishes, cooling, refining of the product.

In one embodiment, FK506 is reacted with Triflate in presence of catalyst(s) to obtain a crude product. Triflate, also known by the systematic name trifluoromethanesulfonate, is a functional group with the formula CF3SO3-.

In an embodiment, Tacrolimus analogues as that disclosed in U.S. Pat. No. 6,387,918 or U.S. Pat. No. 9,505,779 or any other known substitutes of Tacrolimus known to a person skilled in the art at the time of this invention can also be reacted with unsaturated halides according to Heck reaction, to form a similar non-immunosuppressant compound.

In embodiments, an unsaturated halide is an aryl halide or an alkyl halide or an aryl alkyl halide such as but not limited to 9-Iodophenanthrene, 9-Bromophenanthrene, 9-Chlorophenanthrene, 9-Fluorophenanthrene, phenanthrene-9-boronic acid.

In one embodiment, the unsaturated halide is 9-Iodophenanthrene and/or phenanthrene-9-boronic acid.

In the present disclosure, the ratio of FK506 and the unsaturated halide is in equivalents ratio of about 1:1, about 1:1.5, about 1:2, about 1:2.5, about 1:3, about 1:3.5, about 1:4, about about 1:4.5, about 1:5, about 1:6, about 1:7, about 1:8, about 1:9, about 1:10, about 2:1: about about 2:0.5, about 2:3, about 2:5, about 3:1, about 4:1, about 5:1. In one embodiment, the ratio of FK506 and the unsaturated halide is about 1:2. In one embodiment, the ratio of FK506 and the unsaturated halide is about 1:1.5.

In an embodiment, FK506 used in Heck reaction is FK506 hydrate.

In the present disclosure, the ratio of FK506 and the Triflate is in equivalents ratio of about 1:1, about 1:1.5, about 1:2, about 1:2.5, about 1:3, about 1:3.5, about 1:4, about about 1:4.5, about 1:5, about 1:6, about 1:7, about 1:8, about 1:9, about 1:10, about 2:1: about about 2:0.5, about 2:3, about 2:5, about 3:1, about 4:1, about 5:1. In one embodiment, the ratio of FK506 and the Triflate is about 1:2. In one embodiment, the ratio of FK506 and the Triflate is about 1:1.5.

In the present disclosure, the catalyst comprises a base and/or a palladium catalyst.

In embodiments, the catalyst is selected from but not limited to palladium(II) acetate, SPhos, K3PO4, XPhos, CPhos, JohnPhos, DavePhos, BrettPhos, X-Phos, RuPhos, White catalyst, 2,6-dimethyl-p-benzoquinone, dioxane, organic acids such as but not limited to acetic acids, ethers, transition metal coordination complex, triethylamine, Tri-functional N,N,O-terdentate amido/pyridyl carboxylate Pd(II) complexes, N-Heterocyclic Carbene Palladium Complex/Ionic Liquid Matrix, Pd(quinoline-8-carboxylate)2, Triethanolamine base, phosphine-free catalyst or combination thereof. In an embodiment, catalyst employed in this invention as stated above can be in form of catalyst complex and/or captured on a carrier etc. The term "catalyst complex" as used herein relates to a metal organic complex with catalytic activity comprising Pd.

Organic solvent is the higher solvent, such as acetonitrile, dioxane, toluene, p-Xylol, Methyl isobutyl ketone, butylacetate, N-pyrrolidone, N, and dinethylformamide, chlorobenzene etc.

Organic bases are non-coordination organic amine alkali, such as N, and N-dimethyl benzylamine, N-methylmorpholine, N, N-xylidene(s), dimethyl aminopyridine etc.

The reaction of the aromatic compound according to the present invention is carried out at a temperature of from about 20° C. to about 200° C., preferably from about 60° C. to about 160° C., more preferably from about 60° C. to about 120° C.

The reaction time of the present invention is preferably about 30 minutes to about 24 hours, preferably about 2 hour to about 16 hours, more preferably about 2 hours to about 10 hours.

In an embodiments, the yield of purified product is in a range with the lower limit in being from about 20%, about 25%, about 30%, about 35%, about 40%, about 45%, about 50%, about 55%, about 60% with increment of 5% from about 20% to about 60%, and with upper limit about 50% to about 95% in increment of 5% from about 50% to about 90% such that upper limit include about 50%, about 55%, about 60%, about 65%, about 70%, about 75%, about 80%, about 85%, about 90%, about 95% or more. In an embodiment, yield is measured after purification of product in the present disclosure.

In an embodiment, Heck reaction is carried in a sealed vessel.

In an embodiment, crude product of CT474 is extracted from the reacted reaction mixture. The crude product is extracted from the reacted reaction mixture using solvent extraction procedure. Solvent extraction procedure as used herein is Liquid-liquid extraction (LLE). It is a method to separate compounds or metal complexes, based on their relative solubilities in two different immiscible liquids, usually polar and an organic solvent (non-polar). There is a net transfer of one or more species from one liquid into another liquid phase, generally from polar to non-polar. The transfer is driven by chemical potential, i.e. once the transfer is complete, the overall system of chemical components that make up the solutes and the solvents are in a more stable configuration (lower free energy). The solvent that is enriched in solute(s) is called extract. The feed solution that is depleted in solute(s) is called the raffinate. The solvent extraction process can employ organic and/or inorganic solvent, polar and/or non-polar solvent, ionic and/or non-ionic solvent.

In an embodiment, extraction process of CT474 includes solvent extraction and/or distillation method and/or precipitation and/or sublimation and/or dynamic extraction method and/or supercritical fluid extraction, counter current extraction, microwave assisted extraction, ultrasonication-assisted extraction and/or digestion to be done manually and/or by using any instrument like rotary evaporator, freeze drier, supercritical CO2 process and/or any other analytical method known to the person skilled in the art.

In one of the embodiments, purification methods include techniques like various forms of chromatography. 'Chromatography' is an analytical technique commonly used for separating a mixture of chemical substances into its individual components, so that the individual components can be thoroughly analyzed. There are many types of chromatography e.g., liquid chromatography, gas chromatography, ion-exchange chromatography, affinity chromatography such as e.g. silica gel chromatography, Thin layer chromatography, Paper chromatography, High performance liquid chromatography (HPLC), Low performance liquid chromatography (LPLC). The amount that each component of a mixture travels in a chromatography can be quantified using retention factors (Rf). Rf quantify the amount of retardation of a sample in a stationary phase relative to a mobile phase.

In one embodiment, purification method employs vacuum assisted methods, solvent-free methods, sublimation, crystallization, fractional distillation, application, distillation under reduced pressure, steam distillation, differential extraction, filtration, recrystallization.

In another embodiment, silica gel chromatography has been used for purification in the present disclosure.

In embodiments, the anti-fibrotic agent CT474 is to stop or reverse the effects of IPF.

In embodiments, the present invention describes the regulation of the anti-fibrotic agent to the patient or the subject in which CT-474 has been administrated.

In one embodiment, the present disclosure describes the synthetic route to transform FK506 to CT474.

In embodiments of the present disclosure, the factor causing the IPF comprises a bacterial, a viral, a mold, an animal protein, a gene, an age, a gender, an acid reflux, environmental, smoking or exposure to inorganic dust including asbestos, silica, coal dust, beryllium, or hard metal dusts.

The present disclosure also describes methods of treating fibrosis or alleviating the symptoms caused by fibrosis by administering an anti-fibrotic agent described herein in combination with another therapy and drugs known to alleviate the symptoms of fibrosis or IPF.

The present disclosure describes compositions and pharmaceutical compositions including the anti-fibrotic agent that targets the respiratory pathway for administering to cells and subjects. The compositions or pharmaceutical compositions described herein include the anti-fibrotic agent and a carrier or a pharmaceutically acceptable carrier, respectively.

The pharmaceutical compositions described herein include a therapeutically effective amount of the therapeutic anti-fibrotic agent and a pharmaceutically acceptable carrier. The pharmaceutical compositions are formulated to be suitable for the route of administration to a subject. The therapeutic anti-fibrotic agent, such as an anti-fibrotic-agent that targets the cells infected with fibrosis. So, it includes dosage forms to contain a therapeutically effective amount for administration. The pharmaceutical composition including the therapeutic anti-fibrotic agent described herein can be administered in combination with other therapies.

The dosage of the anti-fibrotic agents to be administered to a subject will vary with the precise stage of the fibrosis being treated and the recipient of the treatment. The scaling of dosages for human administration can be performed according to art-accepted practices by a physician depending on various factors. In embodiments, the administration of an amount of anti-fibrotic agent, in a particular dose as well as the interval between doses can depend on the characteristics of the individual, such as general health, age, sex, body weight and tolerance to drugs as well as the type and severity of fibrosis. In embodiments, CT474 can be administered alone or before, along with, or subsequent to administration of the medication(s) used in the ART.

The amount of CT474 thereof to be administered in each dose can be an amount which is effective to produce a desired pharmacokinetic or pharmacodynamic effect.

Methods disclosed herein include treating subjects such as mammals. Examples of mammals include human, chimpanzees, monkeys, dogs, cats, mice, rats, and transgenic species thereof. Subjects in need of a treatment (in need thereof) are subjects infected with fibrosis.

The term "carrier" refers to a diluent, adjuvant (e.g., Freund's adjuvant (complete and incomplete)), excipient, or vehicle with which the therapeutic is administered. Pharmaceutical carriers can be sterile liquids, such as water and oils, including those of petroleum, animal, vegetable or synthetic origin, such as peanut oil, soybean oil, mineral oil, sesame oil and the like. Water is usually used as the carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. For the use of further excipients, please also see "Handbook of Pharmaceutical Excipients", fifth edition, R. C. Rowe, P. J. Seskey and S. C. Owen, Pharmaceutical Press, London, Chicago. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the agent, preferably in purified form, together with a suitable amount of carrier so as to provide the form for proper administration to the patient. The formulation should suit the mode of administration.

The pharmaceutical composition described herein can be formulated into various dosage forms including solid dosage forms for oral administration such as capsules, tablets, pills, powders and granules, liquid dosage forms for oral administration such as pharmaceutically acceptable emulsions, microemulsions, solutions, suspensions, syrups and elixirs, injectable preparations, for example, sterile injectable aqueous or oleaginous suspensions, compositions for rectal or vaginal administration, preferably suppositories.

Pharmaceutical compositions may be administered in a manner appropriate treatment of fibrosis or alleviation of symptoms of fibrosis. The quantity and frequency of administration will be determined by such factors as the condition of the subject, and the type and severity of the fibrosis, although appropriate dosages may be determined by clinical trials.

The administration of the pharmaceutical compositions described herein may be carried out in any convenient manner, including by aerosol inhalation, injection, ingestion, transfusion, implantation or transplantation. The pharmaceutical compositions described herein may be administered to a patient subcutaneously, intradermally, intratumorally, intranodally, intramedullary, intramuscularly, by intravenous (i. v.) injection, or intraperitoneally.

The term "therapeutically effective amount" refers to the amount of an agent that will elicit the biological or medical response of cells, tissue, system, or subject that is being sought by the researcher, veterinarian, medical doctor or another clinician. The term "therapeutically effective amount" includes that amount of a compound that, when administered, is sufficient to alleviate to some extent, one or more of the signs or symptoms of fibrosis. The therapeutically effective amount will vary depending on the agent, the severity and stage of fibrosis, and the age, weight, etc., of the subject to be treated.

By "statistically significant," it is meant that the result was unlikely to have occurred by chance. Statistical significance can be determined by any method known in the art. Commonly used measures of significance include the p-value, which is the frequency or probability with which the observed event would occur if the null hypothesis were true. If the obtained p-value is smaller than the significance level, then the null hypothesis is rejected. In simple cases, the significance level is defined at a p-value of 0.05 or less. A "decreased" or "reduced" or "lesser" amount is typically a "statistically significant" or a physiologically significant amount, and may include a decrease that is about 1.1, 1.2, 1.3, 1.4, 1.5, 1.6 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 1.5, 1.6, 1.7. 1.8, etc.) an amount or level described herein.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability.

The present disclosure is further described by reference to the following exemplary embodiments and examples. These exemplary embodiments and examples are provided for purposes of illustration only and are not intended to be limiting unless otherwise specified. Thus, the present disclosure should in no way be construed as being limited to the following exemplary embodiments and examples, but rather, should be construed to encompass any and all variations which become evident as a result of the teaching provided herein.

EXAMPLES

Microorganisms: *Klebsiella pneumoniae* strain 43816 (American Type Culture Collection, Manassas, Va.) was used for the studies.

Example 1: Synthesis of CT474

Traditional Heck's reaction: To a flame dried microwave vial was added FK506 hydrate (100 mg, 0.1215 mmol, 1 eq.), 9-iodophenanthrene (74 mg, 0.243 mmol, 2 eq.), palladium(II) acetate (3 mg, 0.01215 mmol, 10 mol %), SPhos (10 mg, 0.0243 mmol, 20 mol %), and K3PO4 (51 mg, 0.243 mmol, 2 eq.). Sealed reaction with aluminum cap and purged with nitrogen. Degassed (bubbled with nitrogen gas for 15 min) dioxane (3 mL) was added via syringe and the reaction was heated in the microwave at 80T for 5 h. TLC indicated the presence of multiple UV active products. Diluted reaction with water and extracted with CH2Cl2 three times and EtOAc (ethyl acetate) once. Dried organic layer with Na2SO4 and concentrated in vacuo. The crude was purified via silica gel chromatography with 2% MeOH, 1% NH4OH, 97% DCM solvent mixture. The yield was 59% based on the limiting reactant. The reaction is illustrated in FIG. 1.

Figure 2:
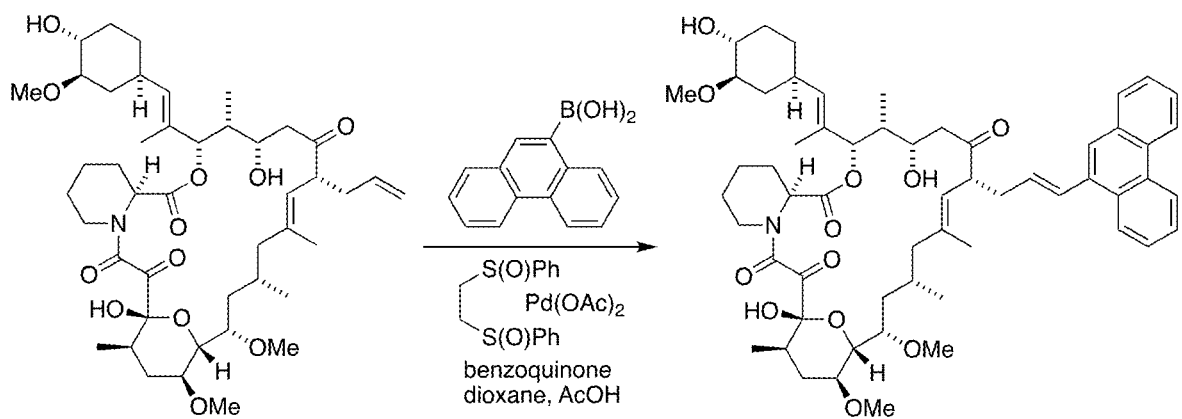
FIG. 2 shows the synthesis of CT-474 from FK-506 by method oxidative Heck reaction. The reactant is FK-506 and the product is CT474.

Oxidative Heck: The procedure was adopted from White et al. (Delcamp, J. H.; Brucks, A. P.; White, M. C. A General and Highly Selective Chelate-Controlled Intermolecular Oxidative Heck Reaction J. Am. Chem. Soc. 2008, 130, 11270-11271): The White Catalyst (CAS: 858971-43-4) was purchased from Strem and stored in dessicator and weighed out in air. ACS Grade 99.7% acetic acid was used. To a screw cap vial in air was added White catalyst (6 mg, 0.01215 mmol, 10 mol %), 2,6-dimethyl-p-benzoquinone (33 mg, 0.243 mmol, 2 eq.), dioxane (1 mL), acetic acid (27.8 µL 0.486 mmol, 4 eq.), FK506 hydrate (100 mg, 0.1215 mmol, 1 eq.), and phenanthrene-9-boronic acid (40 mg, 0.182 mmol, 1.5 eq.) in that order. No flame drying or deoxygenation was done. Let stir at room temperature for 24 h. TLC analysis indicated a new UV active spot with an Rf of 0.56-0.6 in 9:0.9:0.1 DCM-MeOH—NH4OH (Dichloromethane-methanol-ammonium hydroxide). The reaction mixture was diluted with H2O and extracted with CH2Cl2 (2 times). The combined organics were dried over Na2SO4. The mixture was filtered and concentrated in vacuo. The crude was purified via silica gel chromatography with 2.5% MeOH, 1% NH4OH, 96.5% DCM solvent mixture. TLC indicated starting FK506 eluted with desired product. The mixture was subjected to preparatory LC purification using MeCN/water gradient (acetonitrile/water), which was successful in separating the starting material from the product. The yield was 85% based on the limiting reactant. The reaction is illustrated in FIG. 2.

Example 2: In Vitro Characterization of the New Inhibitors

Figure 3:
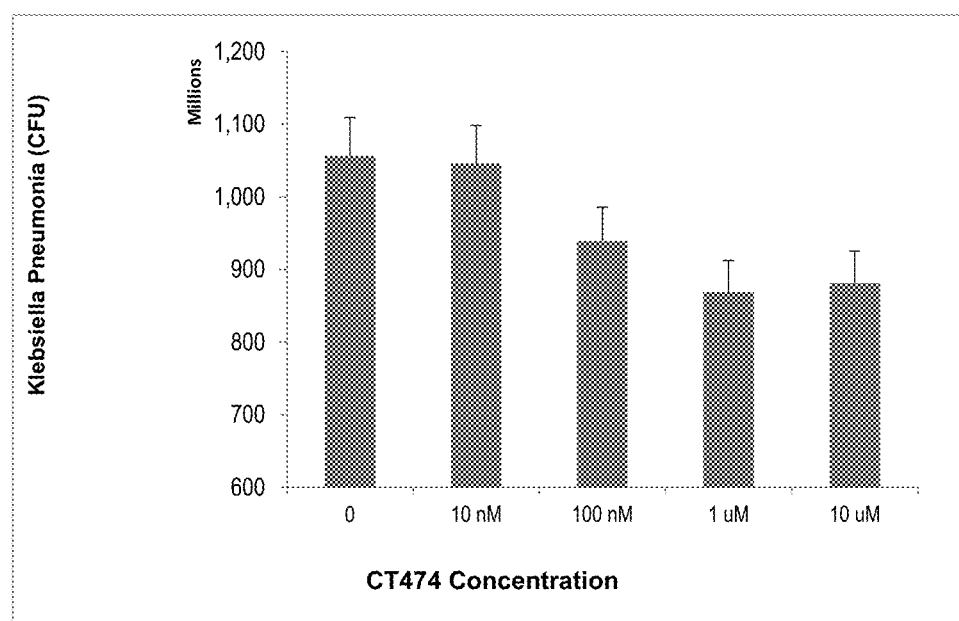
FIG. 3 show CFU of *Klebsiella pneumoniae* cultured in tryptic soy broth at 37° C. for 24 h with 0, 10 nM, 100 nM, 1 µM, and 10 µM CT474 dissolved in 1% Dimethyl sulfoxide (DMSO).

The minimal inhibitory concentration (MIC) method was used to characterize the in vitro efficacy of the compound as shown in the FIG. 3. Briefly, *Klebsiella pneumoniae* strain 43816 (American Type Culture Collection, Manassas, Va.) was grown overnight at 37° C. to mid-log phase in tryptic soy broth. CT474 was initially suspended with DMSO, then diluted in the culture broth with final concentrations of CT474 at 0 nM (1% DMSO alone), 10 nM, 100 nM, 1 µM, and 10 µM with 10,000 CFU *Klebsiella pneumoniae* in 10 mL tryptic soy broth. $OD_{600}$ was measured 24 h later, then the CFU was determined using a standard curve. As shown in FIG. 3 increasing doses of CT474 showed increasingly suppressive effects on the growth of *Klebsiella pneumoniae*.

Statistical calculations were performed using from repeated measures. Analysis of variation (ANOVA) was used to determine differences between groups.

Example 3: Treatment of Mice with CT474

Figure 5:
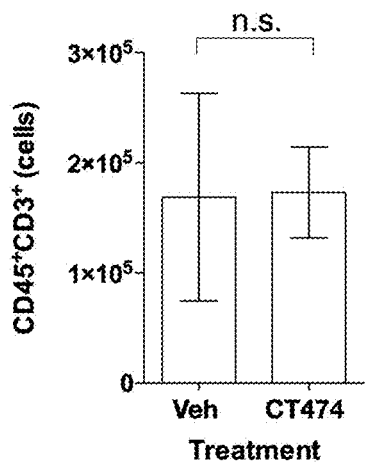
FIG. 5 shows flow cytometry of peripheral blood buffy coat after being treated with either vehicle or CT474. Buffy coat leukocytes were stained with CD45 and CD3 antibodies.
Figure 6:
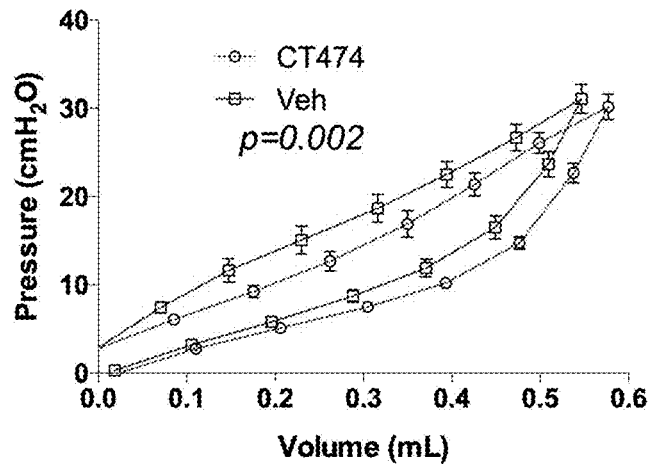
FIG. 6 shows pre-mortem Pressure-Volume curve using Sireq Flexivent in murine lung exposed to bleomycin then treated from days 7 to 13 with vehicle or CT474.
Figure 7:
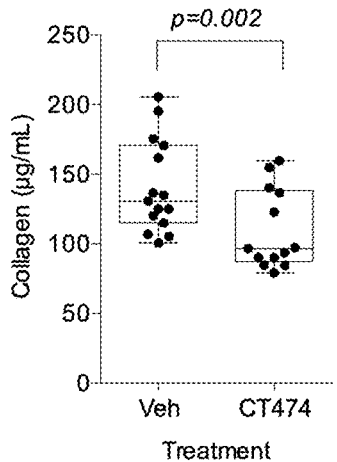
FIG. 7 shows soluble collagen measured by Sircol assay in murine lung (C57B6 WT) exposed to bleomycin then treated from days 7 to 13 with vehicle (n=15) or CT473 (n=13).

Treatment of mice with CT474 in post-disease modeling showed significant reduction in fibrotic lung damage (N=13-15 mice per group, vehicle vs CT474). "Vehicle" as used herein is the substance used as a carrier for the pharmaceutical agent to include aqueous solutions or oils. Oils are derived from petroleum, animal, vegetable or synthetic origin, such as peanut oil. In FIGS. 5-7 signify "veh" signify vehicle. Flow cytometry of peripheral blood buffy coat after being treated with either vehicle or CT474. Buffy coat leukocytes were stained with CD45 and CD3 antibodies is shown in FIG. 5. Pre-mortem Pressure-Volume curve using Sireq Flexivent in murine lung exposed to bleomycin then treated from days 7 to 13 with vehicle or CT474 is shown in FIG. 6. Soluble collagen measured by Sircol assay in murine lung (C57B6 WT) exposed to bleomycin then treated from days 7 to 13 with vehicle (n=15) or CT473 (n=13) is shown in FIG. 7. Statistical calculations were performed using from repeated measures. Analysis of variation (ANOVA) was used to determine differences between groups.

All publications, patents and patent applications cited in this specification are incorporated herein by reference in their entireties as if each individual publication, patent or patent application were specifically and individually indicated to be incorporated by reference. While the foregoing has been described in terms of various embodiments, the skilled artisan will appreciate that various modifications, substitutions, omissions, and changes may be made without departing from the spirit thereof.

REFERENCES

1. Wayn T A, Cellular and molecular mechanisms of fibrosis. *J Pathol.* 2008; 214(2): 199-210. doi:10.1002/path.2277.
2. Paola et al., Adrenomedullin in inflammatory process associated with experimental pulmonary fibrosis. *Respiratory Research*, 2011; 12:41. http://respiratory-research.com/content/12/1/41
3. Wayn et al., Mechanisms of fibrosis: therapeutic translation for fibrotic disease. *Nat Med*, 18(7): 1028-1040. doi:10.1038/nm.2807.
4. Bois et al., An earlier and more confident diagnosis of idiopathic pulmonary fibrosis. *Eur Respir Rev,* 2012; 21: 124, 141-146.doi: 10.1183/09059180.00000812.
5. Baddini-Martinez J et al., Brazilian guidelines for the pharmacological treatment of idiopathic pulmonary fibrosis. Official document of the Brazilian Thoracic Association based on the GRADE methodology. *J Bras Pneumol.* 2020; 46(2):e20190423. doi: https://dx.doi.org/10.36416/1806-3756/e20190423.
6. Delcamp, J. H.; Brucks, A. P.; White, M. C. A General and Highly Selective Chelate-Controlled Intermolecular Oxidative Heck Reaction J. Am. Chem. Soc. 2008, 130, 11270-11271.

The invention claimed is:

1. A method to treat a pulmonary fibrosis comprising administering a compound in a mammalian subject and treating the mammalian subject, wherein the compound is configured to reduce the pulmonary fibrosis in the mammalian subject, wherein the compound comprises a peptidyl-prolyl cis-trans isomerase binding region and a blocked calcineurin binding region, and optionally a solvent accessible region,
wherein the compound is represented by Formula II (Formula II)

2. The method of claim 1, wherein the compound is not an immunosuppressant.

3. The method of claim 1, wherein the peptidyl-prolyl cis-trans isomerase binding region comprises a FKBP binding region.

4. The method of claim 1, wherein the compound is configured to prevent stabilization of collagen leading to the pulmonary fibrosis in the subject.

5. A compound comprising a peptidyl-prolyl cis-trans isomerase binding region and a blocked calcineurin binding region, and optionally a solvent accessible region, wherein the compound is represented by Formula II (Formula II)

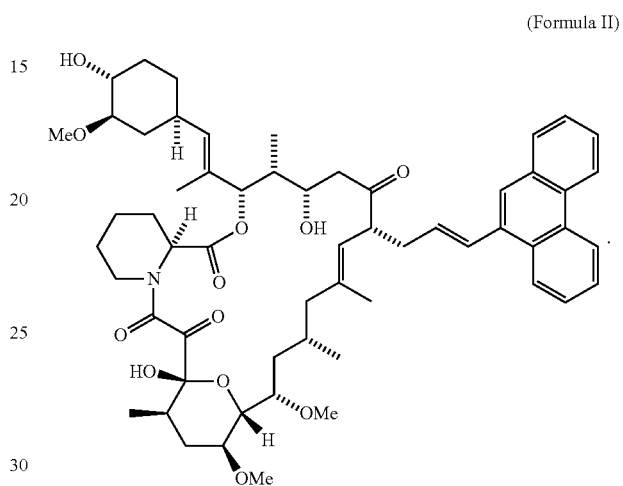

6. The compound of claim 5, wherein the compound is not an immunosuppressant.

7. The compound of claim 5, wherein the peptidyl-prolyl cis-trans isomerase binding region comprises a FKBP binding region.

8. A method comprising: obtaining FK506 or its analogue; and transforming the FK506 or the analogue using a Heck reaction to form a compound represented by Formula II;
wherein the compound synthesized from the transformation using the Heck reaction comprises a FKBP binding region and a blocked calcineurin binding region, and optionally a solvent accessible region;
wherein the Formula II is:

(Formula II)

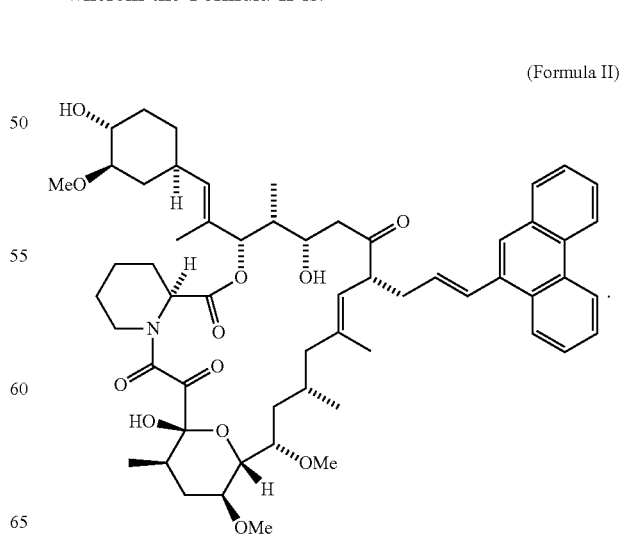

9. The method of claim 8, wherein the Heck reaction is carried in a reaction mixture comprising the FK506 or the analogue, an unsaturated halide and a catalyst comprising Pd.

10. The method of claim 8, wherein the Heck reaction is carried within a temperature range of about 60° C. to about 120° C.

11. The method of claim 9, wherein a yield of the compound extracted from the reaction mixture is within a range of about 50% to about 95%.

12. The method of claim 8, wherein the compound comprises the solvent accessible region.

* * * * *